United States Patent [19]

Keeler et al.

[11] Patent Number: 5,539,638

[45] Date of Patent: Jul. 23, 1996

[54] VIRTUAL EMISSIONS MONITOR FOR AUTOMOBILE

[75] Inventors: James D. Keeler; John P. Havener; Devendra Godbole; Ralph B. Ferguson, II, all of Austin, Tex.

[73] Assignee: Pavilion Technologies, Inc., Austin, Tex.

[21] Appl. No.: 149,216

[22] Filed: Nov. 5, 1993

Related U.S. Application Data

[63] Continuation-in-part of Ser. No. 102,405, Aug. 5, 1993, Pat. No. 5,386,373.

[51] Int. Cl.$^6$ .................................................. F02D 35/00
[52] U.S. Cl. .................. 364/424.03; 60/274; 60/276; 123/672; 364/577; 364/150; 364/151
[58] Field of Search ....................... 364/424.03, 431.03, 364/431.05, 431.06, 149, 151, 497, 498, 499, 577, 578, 431.12, 571.01, 148, 150; 73/117.2, 116; 250/339; 123/571, 672, 674; 60/274, 276; 340/439; 395/912, 913, 914, 915

[56] References Cited

U.S. PATENT DOCUMENTS

| | | | |
|---|---|---|---|
| 3,859,541 | 1/1975 | Hattori et al. | 307/10 R |
| 3,871,338 | 3/1975 | Schmidt et al. | 123/32 EA |
| 3,875,907 | 4/1975 | Wessel et al. | 123/32 EA |
| 3,903,853 | 9/1975 | Kizler et al. | 123/32 EA |
| 3,916,848 | 11/1975 | Schmidt | 123/32 EA |
| 3,919,983 | 11/1975 | Wahl et al. | 123/32 EA |
| 3,962,866 | 6/1976 | Neidhard et al. | 60/276 |
| 4,007,589 | 2/1977 | Neidhard et al. | 60/276 |
| 4,077,207 | 3/1978 | Hattori et al. | 60/276 |
| 4,167,161 | 9/1979 | Nakagami | 123/75 B |
| 4,171,690 | 10/1979 | Hosaka et al. | 123/119 EC |
| 4,245,314 | 1/1981 | Henrich et al. | 364/431 |
| 4,315,243 | 2/1982 | Calvert, Sr. | 340/52 R |
| 4,403,473 | 9/1983 | Gladden | 60/274 |
| 4,438,497 | 3/1984 | Willis et al. | 364/431.05 |
| 4,528,918 | 7/1985 | Sato et al. | 110/347 |
| 4,548,185 | 10/1985 | Pozniak | 123/571 |
| 4,663,703 | 5/1987 | Axelby et al. | 364/149 |
| 4,789,939 | 12/1988 | Hamburg | 364/431.05 |
| 4,853,862 | 8/1989 | Shiraishi et al. | 364/431.05 |
| 5,003,950 | 4/1991 | Kato et al. | 123/422 |
| 5,040,117 | 8/1991 | Shyu et al. | 364/424.03 |
| 5,077,970 | 1/1992 | Hamburg | 60/274 |
| 5,138,163 | 8/1992 | Butler et al. | 250/339 |

(List continued on next page.)

OTHER PUBLICATIONS

Jahnke, Ph.D., James A. 'Continuous Emission Monitoring'. New York: Van Nostrand Reinhold, 1993.

*Primary Examiner*—Kevin J. Teska
*Assistant Examiner*—Russell W. Frejd
*Attorney, Agent, or Firm*—Gregory M. Howison

[57] ABSTRACT

An internal combustion engine [(360)] is provided with a plurality of sensors to monitor the operation thereof with respect to various temperature measurements, pressure measurements, etc. A predictive model processor [(322)] is provided that utilizes model parameters stored in the memory [(324)] to predict from the sensor inputs a predicted emissions output. The model is trained with inputs provided by the sensor and an actual emissions sensor output. During operation, this predicted output on line [(326)] can be utilized to provide an alarm or to be stored in a history database in a memory [(328)]. Additionally, the internal combustion engine [(260)] can have the predicted emissions output thereof periodically checked to determine the accuracy of the model. This is effected by connecting the output of the engine to an external emissions sensor [(310)] and taking the difference between the actual output and the predicted output to provide an error. This is compared to a threshold and, if the error exceeds the threshold, the predictive model processor [(322)] can be placed in a training operation wherein new model parameters are generated. Additionally, retraining could take place external to the predictive model processor [(322)]. During runtime, a control network [(350)] can be utilized to predict control parameters for minimizing the emissions output.

15 Claims, 9 Drawing Sheets

U.S. PATENT DOCUMENTS

| | | | |
|---|---|---|---|
| 5,150,682 | 9/1992 | Magnet | 123/417 |
| 5,163,412 | 11/1992 | Neu et al. | 123/700 |
| 5,177,464 | 1/1993 | Hamburg | 340/439 |
| 5,213,080 | 5/1993 | Lambert et al. | 123/417 |
| 5,220,905 | 6/1993 | Lundahl | 123/681 |
| 5,222,471 | 6/1993 | Stueven | 123/695 |
| 5,228,335 | 7/1993 | Clemmens et al. | 73/118.1 |
| 5,231,939 | 8/1993 | Tanaka | 110/347 |
| 5,247,445 | 9/1993 | Miyano et al. | 364/431.12 |
| 5,271,674 | 12/1993 | Kalmanovitch | 374/16 |
| 5,273,019 | 12/1993 | Matthews et al. | 123/571 |
| 5,349,541 | 9/1994 | Alexandro, Jr. et al. | 364/578 |

VIRTUAL EMISSIONS MONITOR FOR AUTOMOBILE

CROSS REFERENCE TO RELATED APPLICATION

This application is a continuation-in-part of U.S. patent application Ser. No. 08/102,405, filed Aug. 5, 1993, now U.S. Pat. No. 5,386,373 and entitled "VIRTUAL CONTINUOUS EMISSION MONITORING SYSTEM WITH SENSOR VALIDATION".

TECHNICAL FIELD OF THE INVENTION

The present invention pertains in general to emissions monitoring systems, and more particularly, to a system that replaces the continuous emissions monitor on a reciprocating engine with a virtual sensor.

BACKGROUND OF THE INVENTION

As public awareness increases with respect to the environment, industry is required to make significant changes. Although industry is somewhat responsive to public opinion, government regulatory bodies are typically brought in to ensure that public needs are met. In order to do this, government sets up regulatory arms of already existing branches of entities such as the Environmental Protection Agency. These arms are given the task of putting in place policies regarding toxic waste, emissions, etc., that may effect the environment. Further, these regulatory bodies are also given the task of enforcing these regulations. One particular area that has received a great deal of attention in recent years is that of monitoring emissions of noxious gases being placed into the atmosphere by manufacturing facilities.

Typically, the technique for ensuring that noxious gases are being correctly monitored has been to implement Continuous Emissions Monitoring systems (CEM). These systems are utilized to monitor the amount of emissions such as Sulfur Dioxide ($SO_2$), Nitrogen Oxides (NOx), Carbon Monoxide (CO), Total reduced Sulfur (TRS), opacity, Volatile Organic Carbon (VOC), and hazardous substances of all sorts. The classical way of monitoring these emissions is to install a Continuous Emissions Monitor (CEM) in the plant on each emissions point source. Regulatory Agencies provide for each plant guidelines as to how the output is to be regulated, i.e., define the acceptable limit of the emissions. With respect to a reciprocating engine, the EPA has set guidelines as to the performance of the engine. Once manufactured, the engine is expected to meet these guidelines over the life of the engine, assuming that it is properly maintained. However, new regulations are being implemented that require some type of continuous monitoring to be implemented with periodic checkups to ensure that the monitor is operating correctly.

The classic CEM is composed of either an in situ analyzer installed directly in the stack, or the exhaust pipe of the reciprocating engine, or an extractive system which extracts a gas sample and conveys it to an analyzer at grade level. However, these sensors are quite expensive, difficult to maintain, and difficult to keep properly calibrated. As such, the regulations that deal with a CEM system require the sensors to be calibrated frequently, which calibration procedure can take a number of hours, due to the complexity thereof. Regulations allow a maximum downtime of ten percent for calibration. If a unit remains in operation greater than ten percent of the time with the CEM down, the emissions level is considered by the Regulators to be at maximal potential level. This results in out-of-compliance operation. Most manufactures will shut down operation rather than face the high penalties of such occurrence. One of the reasons for this is that the operation of the plant relative to the monitoring of the NOx emissions must be "truly continuous" such that no leeway is provided for faulty sensors, sensors that have fallen out of calibration, etc. One solution to this has been to utilize redundant sensors, which is a very expensive solution. Therefore, there exists a need to provide a system that does not require the presence of a sensor while still ensuring that the output of the plant is within tolerances relative to noxious emissions.

SUMMARY OF THE INVENTION

The present invention disclosed and claimed herein comprises a method for monitoring emissions in an internal combustion engine that emits noxious pollutants and has associated therewith a plurality of sensors for measuring select parameters of the engine operation, these measured parameters provided as sensor output values. A predictive model is provided in which a stored representation of the engine combined with an external emissions monitor is represented. The predictive model is operable to output a predicted emissions value corresponding to the output of the external emissions monitor when attached to the engine, with the inputs to the predictive model corresponding to select ones of the sensor output values. The select ones of the sensor output values are then input to the predictive model and a prediction is provided of the noxious pollutants during operation of the engine without the requirement of the external emissions monitor being connected to the engine. This is achieved during runtime without a runtime monitor for the emissions.

In another aspect of the present invention, the operation of the predictive model is verified by attaching an external emissions monitor to the engine to measure the noxious pollutants output thereby. The measured output is then compared with the predicted output. If the actual and predicted values differ by more than a predetermined amount, the stored representation is adjusted. The stored representation is generated initially by training the predictive model on a training set of data that comprises as input data the actual sensor output values and as target output data the actual measured emissions output of the external emissions monitor. In one method of adjusting the stored representation, the predictive model is retrained to complete a new stored representation on a new set of training data. In another method, the predicted emissions value is merely offset on the output of the predictive model such that the average difference between the offset predicted emissions value and the actual measured emissions value is less than a predetermined difference.

In yet another aspect of the present invention, the predicted emissions value output by the predictive network is compared with an internal threshold value. When the predictive emissions value exceeds the internal threshold value, an alarm is generated. In one embodiment, this alarm is a light. The threshold value can be selected from a plurality of stored threshold values, which threshold value is selected from the plurality of stored threshold values in accordance with predetermined criteria.

In a further aspect of the present invention, a control system is provided for modifying the operating parameters of the engine to adjust the output noxious pollutants. An emissions control system is provided which operates in response to receiving the predicted emissions value output by the predictive model and comparing it with a desired output level. The difference between the two levels is minimized by the control system.

BRIEF DESCRIPTION OF THE DRAWINGS

For a more complete understanding of the present invention and the advantages thereof, reference is now made to the following description taken in conjunction with the accompanying Drawings in which:

FIG. 5b illustrates a detail of the iterate operation of FIG. 5a;

FIG. 6 illustrates a detail of a typical plant, a boiler for a steam generation facility;

DETAILED DESCRIPTION OF THE INVENTION

Figure 1:
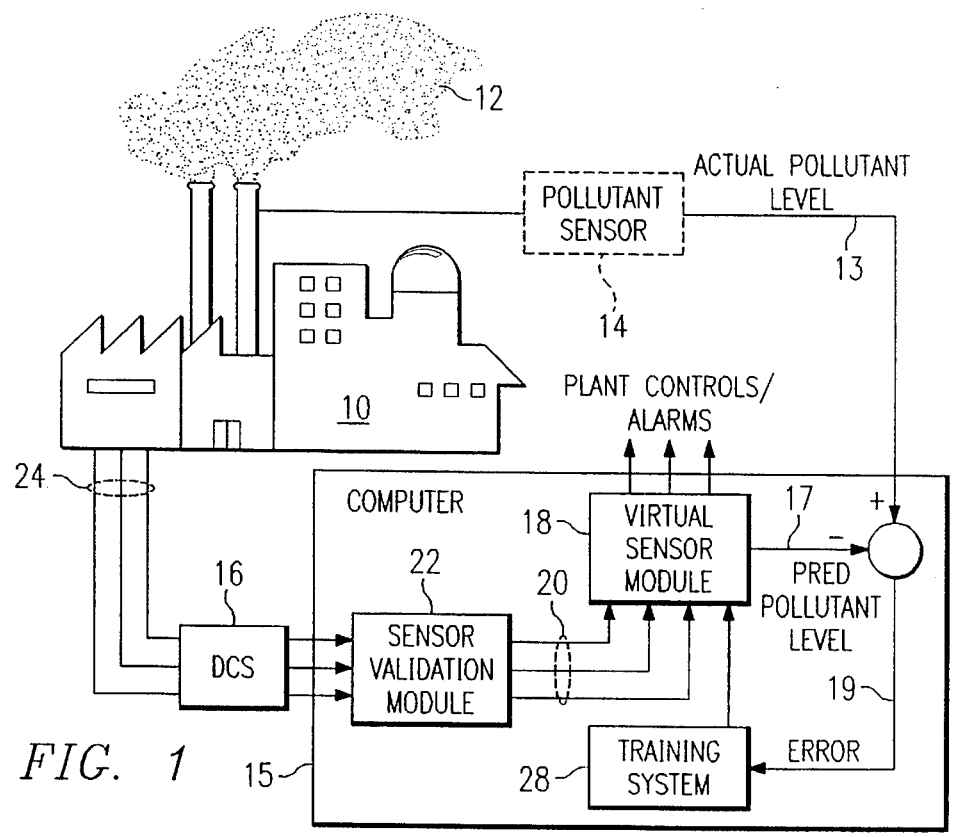
FIG. 1 illustrates an overall block diagram of the virtual sensor of the present invention.

Referring now to FIG. 1, there is illustrated an overall block diagram of the system of the present invention. A plant 10 is provided that, during the normal operation thereof, releases some emissions 12 containing some level of pollutants. The pollutants 12 are monitored by a pollutant sensor 14 or by utilization of EPA established reference methods, which sensor 14 is illustrated in phantom, to provide continuous emissions monitoring. This is referred to as a CEM. As will be described hereinbelow, the present invention provides a virtual sensor operation wherein the pollutant sensor 14 is only required for initial training of virtual sensor network. The pollutant sensor 14 is utilized to gather training data to be combined with the control values and sensor values that are available to a Distributed Control System (DCS) 16, generally referred to as the plant information system. The DCS 16 provides control values associated with control inputs to the system and sensor values to a computer 15. The computer 15 is comprised of a virtual sensor network 18 that essentially provides a non-linear representation of the plant 10, which non-linear representation is a "learned" representation. The virtual sensor network 18 is operable to receive run time inputs 20 from a sensor validation system 22. The sensor validation system 22 is operable to receive actual measured inputs 24 from the plant 10 through the DCS 16. These measured inputs represent measured state variables of the plant in the form of sensor values and also control values that are input to the plant to provide control therefor. As will be described hereinbelow, the various inputs 24 are provided as inputs to the virtual sensor network 18 through the DCS 16. However, some of these inputs may be faulty and the sensor validation system 22 is operable to generate an alarm when any of the attached sensors fails and to replace failed sensor values with reconciled sensor values.

The virtual sensor network 18 is operable to receive the inputs 20 and predict plant controls and alarms. The virtual sensor network 18 can predict what the pollutant levels are that normally would be monitored by the pollutant sensor 14; hence, it provides a virtual sensor. The sensor network 18 is a network that can be trained with a training system 28. The training system 28 utilizes as a target the actual pollutant level on a line 13 as measured by the pollutant sensor 14 when it is present, and also the inputs 24 from the plant 10. The difference between the predicted pollutant level on a line 17 and the actual pollutant level on line 13 generates an error on line 19 that is used by the training system to adjust the stored representation in the virtual sensor module, so as to minimize the error. In operation, as will be described in more detail hereinbelow, the pollutant sensor 14 is a Continuous Emissions Monitor (CEM) that is operable to be temporarily connected to the plant 10 to monitor the level of the pollutants 12. This provides a target to the training system 28. The network 18 is then trained with both the measured plant sensor and control values, not including the CEM output, and the CEM output when present. This information is utilized to generate a training dataset.

After training, the pollutant sensor 14 is removed and then the system operates by predicting what the output of the CEM or pollutant sensor 14 would be. The virtual sensor network 18 then replaces the pollutant sensor 14 and then can be utilized in a control function to predict plant control/ alarms to maintain the operation of the plant 10 within acceptable standards. Further, the virtual sensor network 18 can be used solely to provide an output in place of the pollutant sensor 14 that can be utilized by the operator of the sensor to ensure that all necessary procedures are being followed to ensure that the level of pollutants is within acceptable ranges. For example, if the predicted output from the network 18 exceeded one of the established guidelines or thresholds, the operator would then follow certain prescribed procedures to correct the situation. This would be the case even if the pollutant sensor 14 were present. The advantage to this is that the relatively expensive and difficult to maintain pollutant sensor 14 would not have to be present. Further, a new pollutant sensor 14 or a portable pollutant sensor 14 is periodically utilized to check the operation of a virtual sensor network 18 to ensure that it is operating correctly and that no parameters of the plant have changed such that the prediction is now incorrect or the model no longer represents the plant. In this manner, the system would have to be retrained by using a new set of training data that would be provided by the operation of the connecting the pollutant sensor 14 to the plant 10. This could be the situation wherein some measurement device degraded or the plant itself had physically changed parameters due to capital improvements, age, etc.

In another mode of operation, the pollutant sensor 14 may be in a situation where it might be removed from the plant 10 for calibration purposes. During this time, the virtual sensor network 18 is then utilized to replace the sensor 14 during the calibration procedure.

Figure 1A:
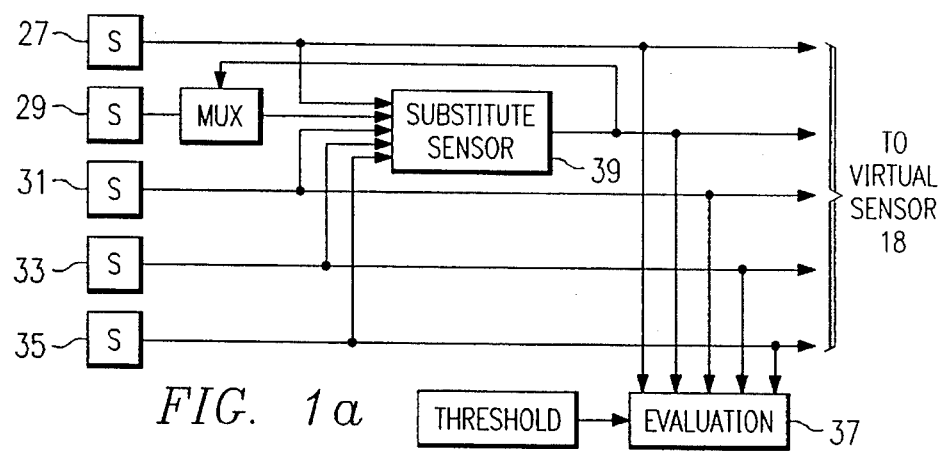
FIG. 1a illustrates a diagrammatic view of the sensor validation system.

Referring now to FIG. 1a, there is illustrated a block diagram of the operation of the sensor validation system 22. A plurality of sensors 27, 29, 31, 33 and 35 are illustrated. Each of the sensors 27, 29, 31, 33 and 35 have an output that is connected to the input of the virtual sensor 18. Additionally, each of the outputs is connected to an evaluation system 37 to determine if the sensor is valid, as will be described hereinbelow. When any one of the sensors 27, 29, 31, 33 and 35 is determined to be faulty, it is replaced by a substitute sensor 39, which is a predicted sensor value that predicts the output of the faulty sensor utilizing a stored representation of the faulty sensor, which stored representation is a function of the other sensors 27, 29, 31, 33 and 35. Therefore, the substitute sensor 39 requires as inputs the outputs of the valid sensors and the predicted output of the substitute sensor. This is illustrated in FIG. 1a with the sensor 29 being substituted, with the substitute sensor 39 receiving as inputs the outputs of the sensors 27, 31, 33 and 35 and, in place of the output of the sensor 29, the predicted output of the substitute sensor 39. Further, another sensor could be substituted for with the output of the substitute sensor 39 being an input for the new and additional sensor (not shown).

Figure 2:
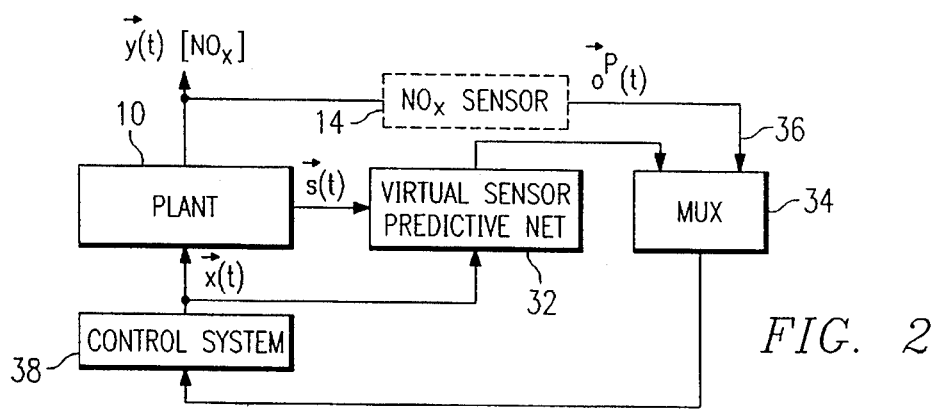
FIG. 2 illustrates a block diagram of the relation of the virtual sensor and the control system.

Referring now to FIG. 2, there is illustrated a block diagram for the operation wherein a virtual sensor predictive network 32 is provided which is operable to receive measured plant sensor values s(t) from the plant 10 and also the control values x(t) which are inputs to the plant 10. The virtual sensor predictive network 32 is operable to output a predicted virtual sensor value $o^p(t)$ for input to a multiplexer 34. The sensor value from sensor 14 is input on the line 36 to the multiplexer 34. The multiplexer 34 is operable to select either the predicted output of the network 32 or the actual output of the sensor 14 for input to a control system 38. The control system 38 is operable to generate the input values x(t) to the plant 10. The multiplexer 34 represents the operation wherein the output of the network 32 is utilized to replace that of the sensor 14.

Figure 3:
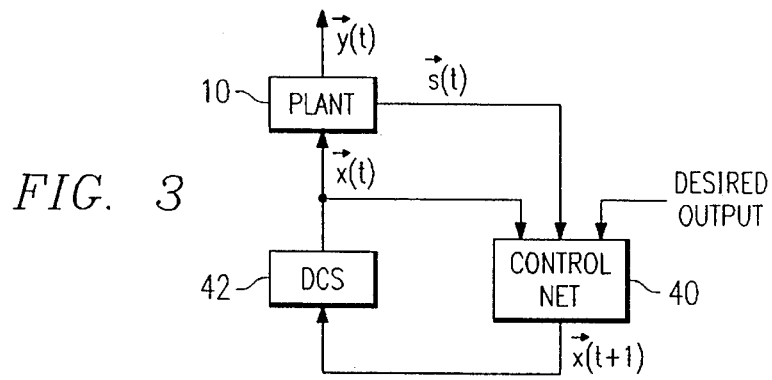
FIG. 3 illustrates an embodiment utilizing a single control network.

Referring now to FIG. 3, there is illustrated one embodiment of the system wherein a dynamic control system is provided. In this system, a control network 40 is provided which receives as an input the control input values x(t) and the sensor values s(t), the sensor values s(t) comprise the measured plant variables such as flow meter measurements, temperature measurements, etc. In addition, the control net 40 is operable to receive a desired output value as one of the inputs. The control net 40 contains a stored representation of the plant and is operable to output a set of control input values x(t+1). These are input to a Distributed Control System (DCS) 42, which is operable to generate the control values x(t). The control network 40 is a conventional control network that is trained on a given desired input, and which control network 40 is operable to receive the sensor values and control values and generate the updated control values x(t+1) that are necessary to provide the desired outputs. The control network 40 is generally comprised of a neural network having associated therewith weights that define the representation that is stored in the neural network. In the embodiment of FIG. 3, these weights are frozen and were learned by training the control network 40 on a given desired output with a given set of training data for the control values x(t) and the sensor values s(t). A desired output is provided as one input for selecting between sets of weights. The general operation of control nets is described in W. T. Miller, III, R. S. Sutton and P. J. Werbos, "Neural Networks for Control", *The MIT Press*, 1990, which reference is incorporated herein by reference.

Figure 4:
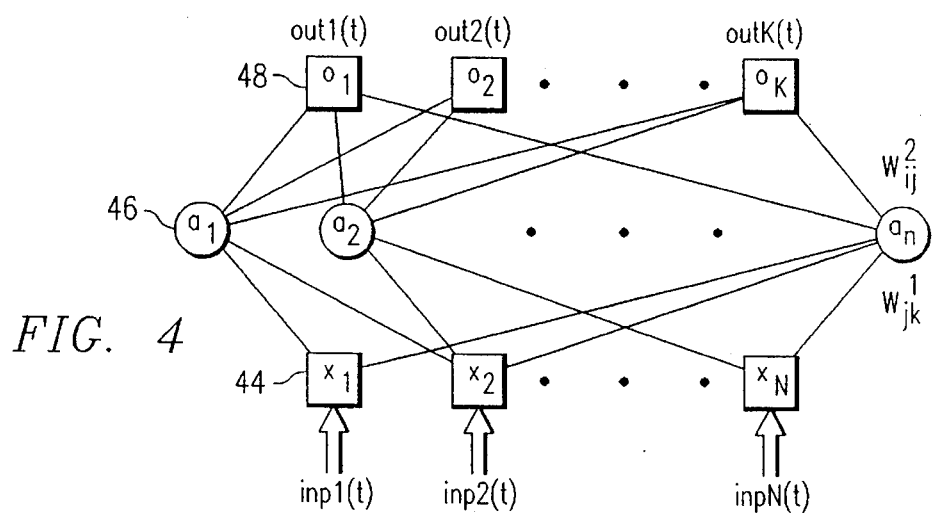
FIG. 4 illustrates a diagrammatic view of a conventional neural network.

Referring now to FIG. 4, there is illustrated a detailed diagram of a conventional neural network comprised of input nodes 44, hidden nodes 46 and output nodes 48. The input nodes 44 are comprised of N nodes labelled $x_1, x_2, \ldots x_N$, which are operable to receive an input vector x(t) comprised of a plurality of inputs, INP1(t), INP2(t), ... INPN(t). Similarly, the output nodes 48 are labelled $o_1, o_2, \ldots o_K$, which are operable to generate an output vector o(t), which is comprised of the output OUT1(t), OUT2(t), ... OUTK(t). The input nodes 44 are interconnected with the hidden nodes 46, hidden nodes 46 being labelled $a_1, a_2, \ldots a_n$, through an interconnection network where each input node 44 is interconnected with each of the hidden nodes 46. However, some interconnection schemes do not require full interconnection. Each of the interconnects has a weight $W_{ij}^1$. Each of the hidden nodes 46 has an output $o_i$ with a function g, the output of each of the hidden nodes defined as follows:

$$\vec{a_j} = g \left( \sum_{i=1}^{N} W_{ij}^1 x_i + b_j^1 \right) \quad (1)$$

Similarly, the output of each of the hidden nodes 46 is interconnected with substantially all of the output nodes 48 through an interconnect network, each of the interconnects having a weight $W_{jk}^2$ associated therewith. The output of each of the output nodes is defined as follows:

$$\vec{O_k} = g \left( \sum_{j=1}^{n} W_{jk}^2 a_j + b_k^2 \right) \quad (2)$$

This neural network is then trained to learn an function f(x(t), P) as follows:

$$\vec{o}(t) = \vec{f}(\vec{x}(t), \vec{P}) \quad (3)$$

where o(t) is an output vector and P is a vector or parameters ("weights") that are variable during the learning stage. The goal is to minimize the Total-Sum-Square-Error function:

$$\vec{E} = \sum_{t=1}^{M} (\vec{y}(t) - \vec{O}(t))^2 \quad (4)$$

The Total-Sum-Square-Error function is minimized by changing the parameters P of the function f. This is done by the back propagation or a gradient descent method in the preferred embodiment on the parameters $W_{jk}^2, W_{ij}^1, b^{1j}, b^{2k}$. This is described in numerous articles, and is well known. Therefore, the neural network is essentially a parameter fitting scheme that can be viewed as a class of statistical algorithms for fitting probability distributions. Alternatively, the neural network can be viewed as a functional approximator that fits the input-output data with a high-dimensional surface. The neural network utilizes a very simple, almost trivial function (typically sigmoids), in a multi-layer nested structure The neural network described above is just one example. Other types of neural networks that may be utilized are those using multiple hidden layers, radial basis functions, gaussian bars (as described in U.S. Pat. No. 5,113,483, issued May 12, 1992, which is incorporated herein by reference), and any other type of general neural network. In the preferred embodiment, the neural network utilized is of the type referred to as a multi-layer perceptron.

Figure 5A:
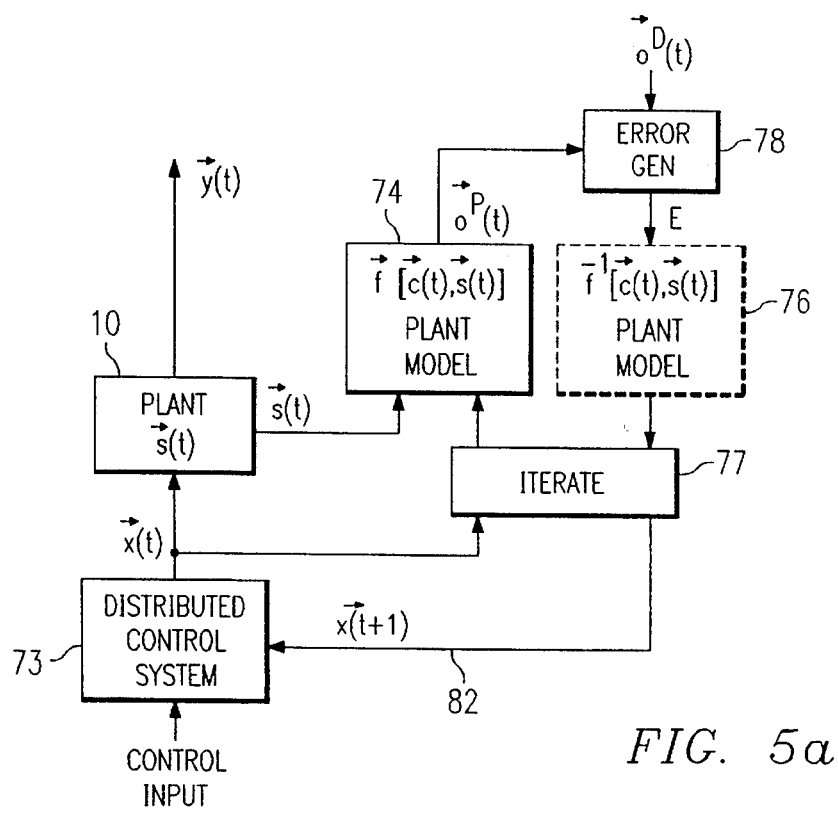
FIG. 5a illustrates a more detailed block diagram of the control network.

Referring now to FIG. 5a, there is illustrated a block diagram of a control system for optimization/control of a plant's operation. The plant 10 has an input for receiving the control values $x(t)$ and an output for providing the actual output $y(t)$ with the sensor values $s(t)$ being associated therewith, these being the internal state variables. A plant predictive model 74 is developed with a neural network to accurately model the plant in accordance with the function $f(x(t),s(t))$ to provide an output $o^p(t)$, which represents the predicted output of plant predictive model 74. The inputs to the plant model 74 are the control values $x(t)$ and the sensor values $s(t)$. For purposes of optimization/control, the plant model 74 is deemed to be a relatively accurate model of the operation of the plant 72. In an optimization/control procedure, an operator independently generates a desired output value $o^d(t)$ for input to an error generation block 78 that also receives the predicted output $o^p(t)$. An error is generated between the desired and the predicted outputs and input to an inverse plant model 76 which is identical to the neural network representing the plant predictive model 74, with the exception that it is operated by back propagating the error through the original plant model with the weights of the predictive model frozen. This back propagation of the error through the network is similar to an inversion of the network with the output of the plant model 76 representing a $\Delta x(t+1)$ utilized in a gradient descent operation illustrated by an iterate block 77. In operation, the value $\Delta x(t+1)$ is added initially to the input value $x(t)$ and this sum then processed through plant predictive model 74 to provide a new predicted output $o^p(t)$ and a new error. This iteration continues until the error is reduced below a predetermined value. The final value is then output as the new predicted control values $x(t+1)$.

This new $x(t+1)$ value comprises the control values that are required to achieve the desired actual output from the plant 72. This is input to a control system 73, wherein a new value is presented to the system for input as the control values $x(t)$. The control system 73 is operable to receive a generalized control input which can be varied by the distributed control system 73. The general terminology for the back propagation of error for control purposes is "Back Propagation-to-Activation" (BPA).

In the preferred embodiment, the method utilized to back propagate the error through the plant model 76 is to utilize a local gradient descent through the network from the output to the input with the weights frozen. The first step is to apply the present inputs for both the control values $x(t)$ and the sensor values $s(t)$ into the plant model 74 to generate the predicted output $o^p(t)$. A local gradient descent is then performed on the neural network from the output to the input with the weights frozen by inputting the error between the desired output $o^d(t)$ and the predicted output $o^p(t)$ in accordance with the following equation:

$$\Delta c(t) = c(t+1) - c(t) = \eta \frac{\partial (o^d(t) - o^p(t))^2}{\partial c(t)} \tag{5}$$

where $\eta$ is an adjustable "step size" parameter. The output is then regenerated from the new $x(t)$, and the gradient descent procedure is iterated.

Figures 5B, 6:
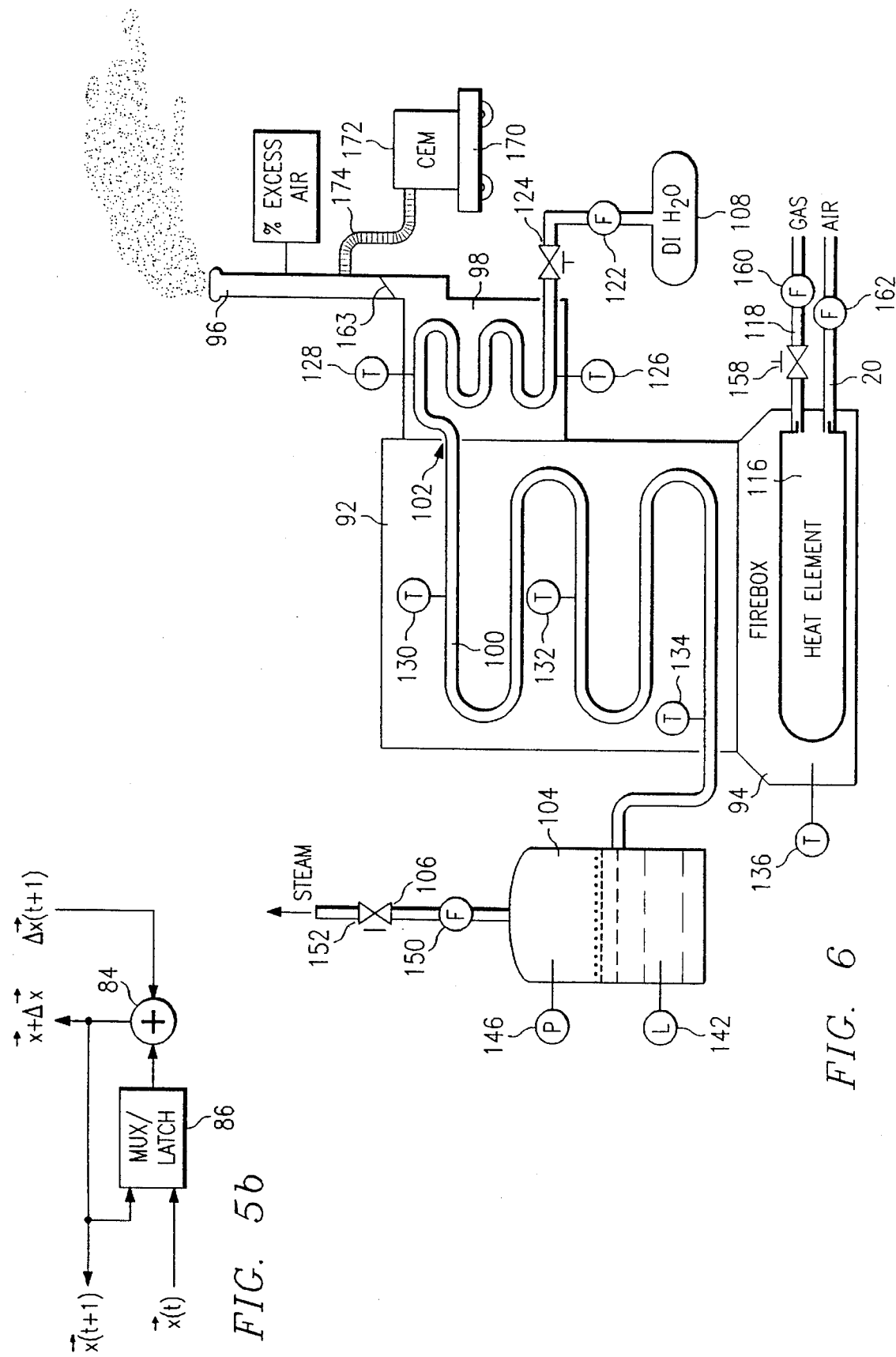

Referring now to FIG. 5b, there is illustrated a detailed block diagram of the iterate block 77. The iterate block 77 is comprised of a summing junction which is operable to receive the $\Delta x(t+1)$ input and the output of a multiplexor/latch block 86. The multiplexor/latch block 86 is operable to receive both the output of the summing junction 84 for feedback as one of the inputs and the control variable $x(t)$. The output of the summing block 84 is the sum of the previous value of $x(t)$ plus the new iterative change value $\Delta x(t)$. This will then be iteratively summed with the previous value to generate a new iterative value until the error is at a predetermined level. At this point, the output of the summing junction 84 will comprise the new control value $x(t+1)$.

Another standard method of optimization involves a random search through the various control values to minimize the square of the difference between the predicted outputs and the desired outputs. This is often referred to as a monte-carlo search. This search works by making random changes to the control values and feeding these modified control values into the model to get the predicted output. The predicted output is then compared to the desired output and the best set of control values is tracked over the entire random search. Given enough random trials, a set of control values will be obtained that produces a predicted output that closely matches the desired output. For reference on this technique and associated, more sophisticated random optimization techniques, see the paper by S. Kirkpatrick, C. D. Gelatt, M. P. Vecchi, "Optimization by Simulated Annealing". *Science*, vol. 220, 671–780 (1983), which reference is incorporated herein by reference.

Referring now to FIG. 6, there is illustrated a diagrammatic view of a typical plant that may exist at a manufacturing facility. The plant typically comprises a boiler 92 which has a firebox 94 disposed at the lower end thereof. The boiler 92 interfaces with a stack 96 through a preheat chamber 98. Many tubes of which tube 100 is typical thereof are operable to run through the chamber 98 and enter the boiler 92. The tube 100 then passes in a serpentine manner through the boiler 92 to an output pressure vessel 104, which is pressurized. The vessel 104 is operable to generate steam out of an outlet 106. The other end of the tube 100 that enters the chamber 98 is connected to a source 108 of the deionized water. In operation, the water is passed through the tube 100 to the chamber 98, which picks up heat therein and then into the main boiler 92, where it is heated further. This then passes through to the vessel 104. The firebox 94 has a heating element 116 associated therewith that is operable to receive gas through a gas line 118 and air through an air line 120. The mixture of the gas and the air allows the heating element 116 to generate heat in the firebox 94 and heat up the water in the tube 100 within the boiler 92.

The tube 100, when it exits the source 108 with the deionized water at the source, has the flow thereof measured by the flow meter 122. A valve 124 allows control of the flow of fluid from the source 108 into the chamber 98. Two temperature sensors 126 and 128 are provided at different locations along the tube 100 within the chamber 90 to provide temperature measurements therefor. Additionally, temperature sensors 130, 132 and 134 are provided along the tube 100 at various locations within the main boiler 92. A temperature sensor 136 is provided for the firebox 94. The level of the fluid within the pressure vessel 104 is measured by a level meter 142 and the pressure therein is measured by a pressure meter 146. A flow meter 150 is provided for measuring the flow of steam out of the pressure vessel and a control valve 152 provides control of the steam exiting the pressure vessel 104. The heater element 116 is controlled with a valve 158 on the gas line, which has the flow thereof measured by a flow meter 160. The flow meter on the air line 120 is measured by a flow meter 162. A damper 163 in the stack 96 is utilized to control air flow through the firebox 94.

It can be seen that the sensor values s(t) of the plant are provided by the various temperature and flow measurement devices. Further, the control values, in the form of the various valves and damper positions provide the control values to the plant. Therefore, an operator can control the operation of the plant by controlling the various flow meters and other control values, some of which are not illustrated. The remaining inputs that are necessary in order to provide adequate control of the plant for the purpose of continuous emissions monitoring are the NOx levels. These are provided by the virtual sensor network 18 of FIG. 1. However, as described above, periodically a portable unit 170, having disposed thereon a CEM 172, is connected via a duct 174 to the stack 96 to measure the amount of NOx in the output emissions to the air. The CEM 172 then generates a report as to the level of the NOx. If this level is within acceptable standards, then this is merely reported. However, if the level is outside of acceptable limits, this is reported to the plant operator and either changes are made or the plant is shut down. Additionally, the information generated by the CEM 172 is generated on a time base and this comprises training data. This training data, since it is on a common time base, can then be combined or merged with data associated with the sensor values and the control values, which are also on a time base, to provide new training data for the virtual sensor network 18. This can be utilized by the training system 20 to retrain the virtual sensor network 18, if necessary.

Figure 7:
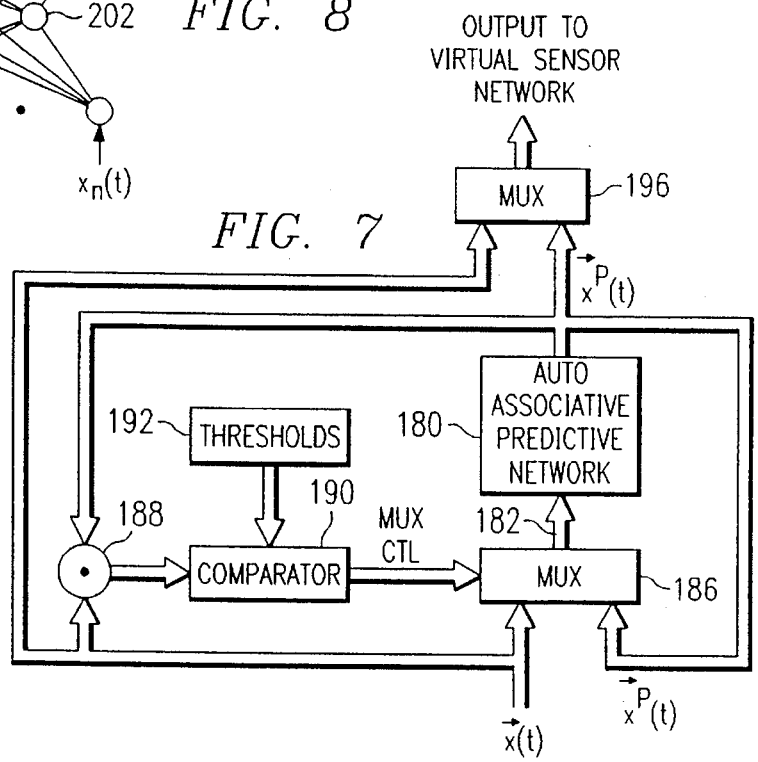
FIG. 7 illustrates a block diagram of the sensor validation network.

Referring now to FIG. 7, there is illustrated a block diagram of the preferred embodiment for the sensor validation system 22. To ensure that the overall inputs x(t) to the network 18 are "valid", it is necessary to perform some type of comparison with expected or predicted values. If it is suspected that the generated values are not accurate, then an alarm is generated to advise the plant operator or the control system of the need to calibrate the sensor or to repair the sensor, and an estimated or predicted value for that sensor value is substituted for the actual measured value of the sensor.

In a preferred embodiment, an auto associative predictive neural network 180 is provided which is a network having an input layer for receiving select ones of the inputs x(t) on an input 182. Although not illustrated, only certain ones of the actual sensor values are necessary as inputs to the virtual sensor network 18 in order to provide an accurate prediction of the NOx levels that would generally be provided by the pollutant sensor 14. These are determined by performing a sensitivity analysis. This is described in U.S. patent application Ser. No. 056,197, filed Apr. 30, 1993 and entitled "Method and Apparatus for Determining the Sensitivity of Inputs to a Neural Network on Output Parameters" (Atty. Dkt. No. PAVI-21,761), which is assigned to the present Assignee. By utilizing the sensitivity analysis, the number of inputs to the network 18 can be significantly reduced and only the important inputs utilized. This significantly reduces the size of the auto associative predictive network 180 and also the virtual sensor network 18.

The actual inputs x(t) are input to a multiplexer 186 which is operable to select between the predicted inputs $x^P(t)$ output by the network 180, which is a predicted output, and the actual inputs x(t). In operation, a first cycle occurs when the multiplexer selects the actual inputs x(t). The predicted inputs $x^P(t)$ are then input to a subtraction circuit 188 to determine the difference between x(t) and $x^P(t)$. This difference is input to comparator 190 for comparison with thresholds stored in a threshold memory 192. The one of the actual inputs to the network 180 having associated therewith the largest error as compared to the acceptable threshold is then connected to the associated predicted output of the network 180. The actual inputs x(t) with the substituted or reconnected input is then again cycled through the auto associative predictive network 180. On this next cycle, the difference between the actual and the predicted values are again determined, compared with the thresholds, and the one of the actual inputs having the largest error is reconnected to the associated predicted input by the multiplexer 186. This continues until all of the predicted inputs, with the determined faulty or unacceptable actual values replaced with the predicted values output by the network 180, are within a predetermined range. Once this has occurred, the predicted values from the network 180 are input to a multiplexer 196, and the multiplexer 196 selecting for output therefrom the actual values that were determined to be acceptable and the predicted values as a substitute for the actual values that were determined to be unacceptable. It should be noted that the predicted values are generated by running the network with the determined unacceptable actual values replaced with the associated predicted values by the multiplexor 186. The output of the multiplexor 196 is then input to the virtual sensor network 18.

In another embodiment, the predicted input values output by the auto associative predictive network 180 can be provided as the input to the virtual sensor network 18. This would then not require the multiplexer 196 and, in fact, the auto associative predictive network 180 can continually monitor and replace ones of the sensor inputs that are determined to be invalid.

Figure 8:
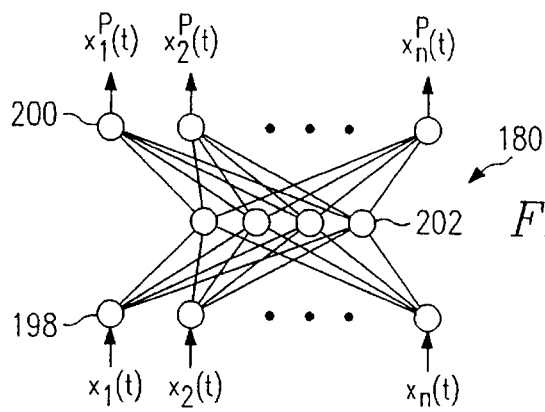
FIG. 8 illustrates a diagrammatic view of the auto associative predictive network utilized in the system of FIG. 7.

Referring now to FIG. 8, there is illustrated a diagrammatic view of the auto associative predictive network 180. The network is comprised of an input layer of nodes 198 and an output layer of nodes 200. There is one node in the layer 198 for each of the input vectors x(t), illustrated as $x_1(t)$, $x_2(t) \ldots x_n(t)$. Similarly, there is a single node for each of the predicted output variables $x^P(t)$ such that there are outputs $x_1^P(t), x_2^P(t) \ldots X_A^P(t)$. The input layer of nodes 198 is mapped through to the output layer of nodes 200 through a hidden layer of nodes 202. The hidden layer of nodes 202 has a plurality of interconnections with each of the nodes in the input layer of nodes and each of the output layer of nodes 200. Each of these interconnections is weighted. Further, the number of nodes in the hidden layer of nodes 202 is less than the number of nodes in either the input layer 198 or the output layer 200. This is therefore referred to as a bowtie network. The network 180 can be trained via a back propagation training technique. This is described in D. E. Rumelhart, G. E. Hinton and R. J. Williams, "Learning Internal Representations by Propagations" in D. E. Rumelhart and J. L. McClelland, *Parallel Distributive Processing*, Vol. 1, 1986.

Figure 9A:
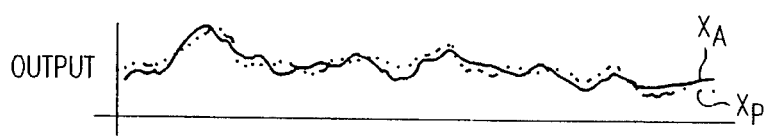
FIGS. 9a and 9b illustrate plots of predicted versus actual pollutant sensor values and the difference therebetween.
Figure 9B:

Referring now to FIGS. 9a and 9b, there are illustrated two plots depicting operation of the sensor validation system 22. The actual inputs are represented by $X_A$ and the predicted input is represented by $X_p$. It can be seen that the predicted input does not exactly follow the actual input, it being noted that the actual input is actually the input to the overall system. The difference between the actual and the predicted input values is illustrated in FIG. 9b.

Figure 10A:
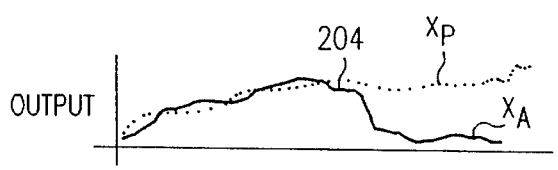
FIGS. 10a and 10b illustrate the plots of FIGS. 9a and 9b, respectively, wherein one of the sensors is faulty.
Figure 10B:
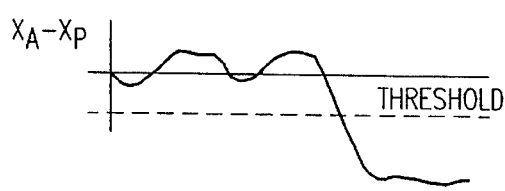

Referring now to FIGS. 10a and 10b, there is illustrated corresponding plots to those of FIGS. 9a and 9b with the exception that the sensor generating the actual input fails. It can be seen that up to a point 204 on the curve $X_a$, the predicted and actual sensor values track fairly well with minimal error. However, at the point 204 the error increases dramatically, indicating that the sensor no longer provides an value that corresponds to the predicted value. This is illustrated in FIG. 10b, wherein the error increases. When the difference between $X_A$ and $X_p$ is greater than a threshold, this indicates an invalid reading. However, as noted above, only the one of the sensors having the highest error above the threshold will be selected as replacement value by the multiplexer 86 for the next cycle. This is due to the fact that the network 180 is trained on all of the input variables and each of the input variables will affect the predicted values for the remaining ones. Therefore, if the actual input values associated with predicted output values having an error greater than the threshold were replaced, this would not be as accurate as iteratively replacing one at a time.

Figure 11:
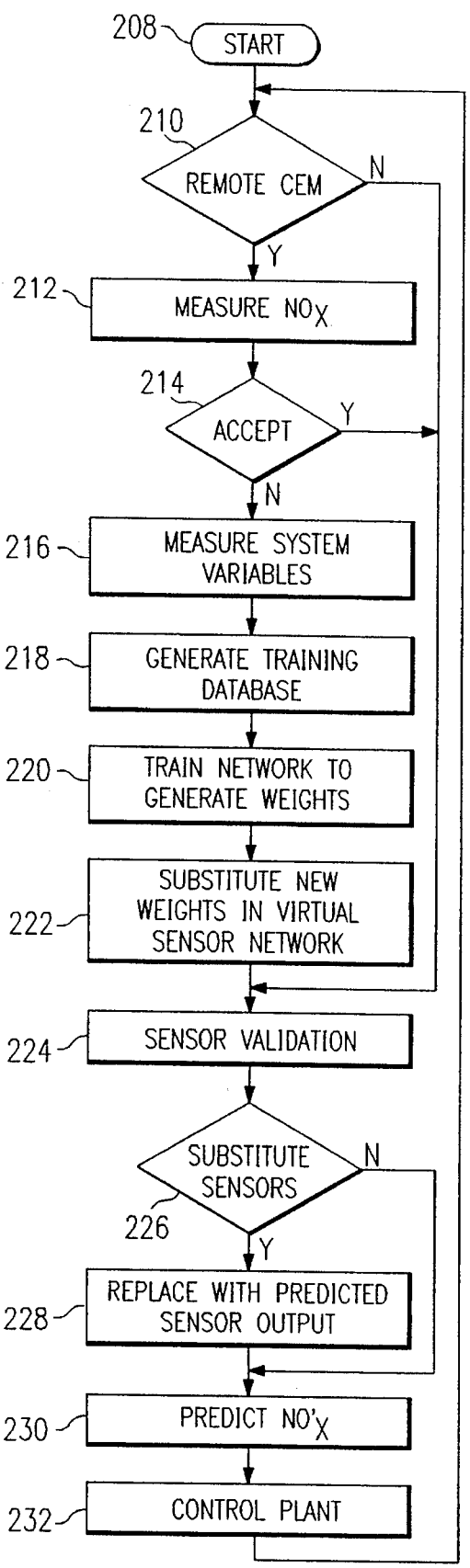
FIG. 11 illustrates a flowchart for operating the overall system.

Referring now to FIG. 11, there is illustrated a flowchart depicting the overall operation of the system. The flowchart is initiated at a start block 208 and then flows to a decision block 210. Decision block 210 determines whether the remote CEM has been installed. If so, the program then flows to a function block 212 to measure the NOx levels with the remote CEM. The program then flows to a decision block 214 to determine whether the measured NOx values, measured in function block 212, are acceptable. If not, this indicates that the virtual sensor network 18 is out of spec and that the system has either changed or the network no longer represents the system. The program will then flow along an "N" path to a function block 216 to measure the system variables and then to a function block 218 to generate a training database. A training database essentially utilizes the system variables that are measured along the same time base as the measured NOx levels. Typically, the remote CEM will be placed adjacent to the manufacturing facility and the pollutants measured for a predetermined amount of time, which can be measured in hours, days or weeks. At the same time, the plant facility itself is measuring the plant variables. These are also placed on a time base and stored. By merging the two data sets, a training database can be provided for training the virtual sensor network 18. This time merging operation is described in U.S. patent application Ser. No. 07/980,664, filed Nov. 24, 1993 and entitled "Method and Apparatus for Operating a Neural Network with Missing and/or Incomplete Data".

Once the training database has been generated, the virtual sensor network 18 is trained, as indicated by a function block 220. This essentially generates weights, which can then be substituted for the neural network weights in the virtual sensor network 18. The program then flows to a function block 222 to substitute new weights in the virtual sensor network 18. Thereafter, the program flows to a main operating portion of the program, which is initiated at a function block 224 to validate the sensors.

If the pollutant parameters measured in the function block 212 were acceptable, the program would flow from the decision block 218 along a "Y" path to the input of function block 224 to bypass the training step. Additionally, if the remote CEM is not present, the program would flow along an "N" path from the decision block 210 to the input of the sensor validation block 224.

The sensor validation block 224 validates the sensors and, if one is found invalid, it substitutes a predicted value for that invalid sensor. The program would then flow to a function block 226 to determine if certain sensors needed to be replaced by predicted values. If so, the program would flow along a "Y" path to replace the invalid sensors with the predicted sensor value. The program would then flow to a function block 232 to predict the pollutant value and then to a function block 232 to control the plant. The program would then flow back to a decision block 210. If it were determined that sensors did not need to be replaced by their predicted values, the program would flow along an "N" path from the decision block 226 to the input of function block 230.

Figure 12:
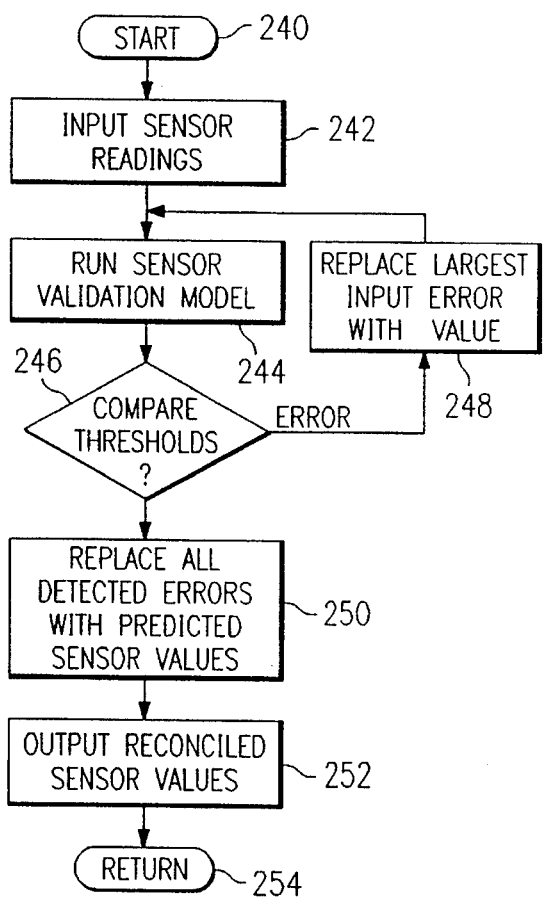
FIG. 12 illustrates a flowchart for the sensor validation operation.

Referring now to FIG. 12, there is illustrated a function block depicting the operation of the sensor validation. The program is initiated at a start block 240 and then flows to a function block 242 to input the various sensor readings. The program then flows to a function block 244 to run the sensor validation model and then to a decision block 246 to compare the predicted input values with the thresholds and generate an error signal when any of the predicted input values exceed the thresholds for that given variable, it being noted that there can be a threshold for each variable as to what constitutes an error for that sensor value. When an error exists, the program flows to a function block 248 to replace the largest input error with the mean value for that input. An alarm is generated at this point to warn of the failed sensor. The program will then flow back the input of a function block 244.

When the system has iteratively determined that there are no longer any predictive outputs that exceed these thresholds, the program will flow from a decision block 246 to a function block 250 to replace all detected errors with predicted sensor values and then to a function block 252 to output reconciled sensor values. The program will then flow to a return block 254.

Figure 13:
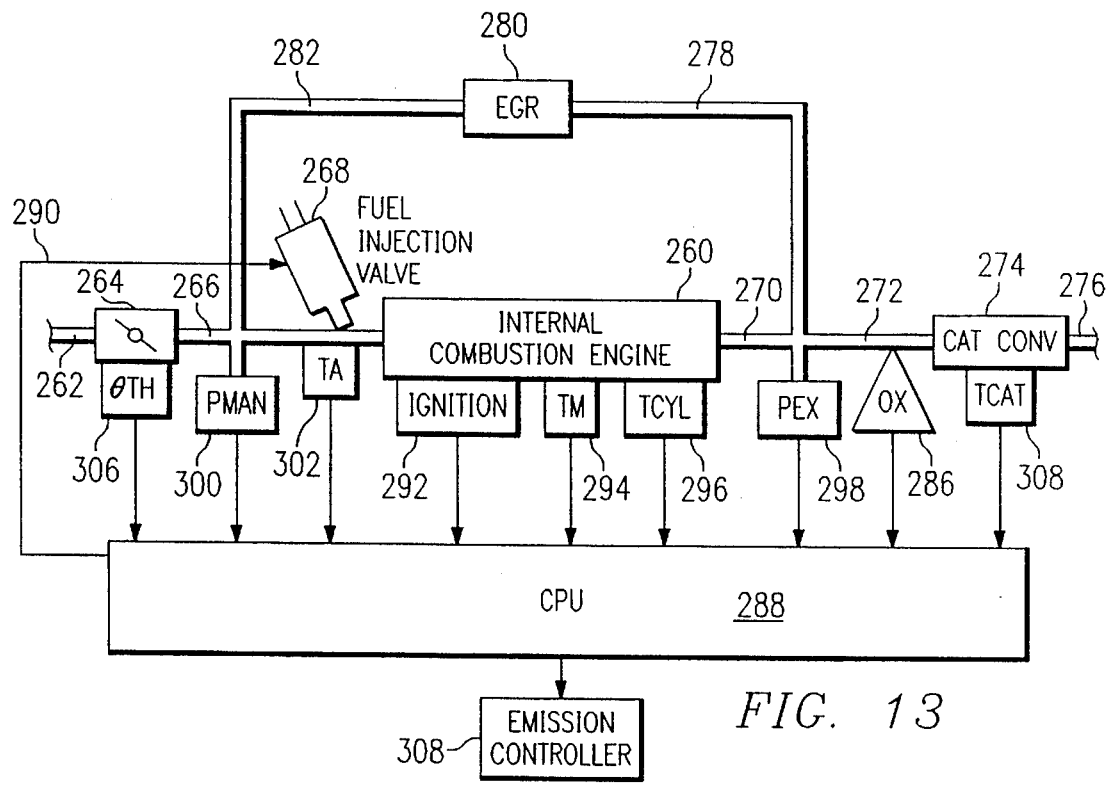
FIG. 13 illustrates the preferred embodiment of the present invention wherein the virtual sensor is utilized in conjunction with an internal combustion engine.

Referring now to FIG. 13, there is illustrated an embodiment wherein the virtual sensor is utilized in conjunction with an internal combustion engine 260. The internal combustion engine 260 receives air on an intake port 262. This is input to a butterfly valve 264 which is basically the throttle valve that is controlled by the foot pedal on an automobile. The butterfly valve then feeds the restricted airflow to an intake manifold 266, which is input to the internal combustion engine 260. A plurality of fuel injection valves, only one of which is illustrated, fuel injection valve 268. The fuel injection valve 268 is operable to inject fuel into the intake manifold 266 in a regulated amount, which is determined by a number of factors, this being conventional. The internal combustion engine 260 exhausts the combustion ingredients into an exhaust manifold 270. The exhaust manifold 270 is connected to an exhaust pipe 272 which is connected to the input of a catalytic converter 274. The catalytic converter 274 then interfaces with the tail pipe 276 to output the combustion gases.

The exhaust manifold 270 is connected through a pipe 278 to an emissions gas recirculation valve (EGR) 280. The EGR 280 is interfaced with the intake manifold 266 through a pipe 282. The EGR 280 is a conventional pollution control device that is operable to bleed off a small portion of the exhaust gases from the exhaust manifold 270 back into the intake manifold for recombustion thereof. EGR valves typically operate at higher RPMs of the engine, as the recirculation of the exhaust gases at low RPMs causes the engine to idle roughly.

In typical internal combustion engines, an oxygen sensor 286 is disposed in the exhaust manifold 270. The oxygen sensor 270 basically provides for measurement of the exhaust gas ingredient concentration, typically oxygen, that exists in the exhaust manifold 270. These type of sensors are utilized for air-fuel ratio control systems. The sensor is input to a central processing unit (CPU) 288 which controls the operation of the fuel injectors through a line 290 and the fuel supply thereto. Again, these are conventional systems.

In addition to the oxygen sensor 286, the CPU 288 is operable to monitor a large number of parameters regarding the internal combustion engine, which parameters require some type of sensors. In the example illustrated in FIG. 13, the operation of the ignition, i.e., spark advance, timing, etc., is provided to an ignition module 292. The manifold temperature is provided by a manifold temperature sensor (TM) 294 and the cylinder temperature is provided by a cylinder temperature sensor (TCYL) 296. The sensors 294 and 296 allow a temperature measurement to be made of each cylinder and the overall manifold. The back pressure in the exhaust pipe 270 is provided by a pressure sensor (PEX) 298 and the pressure in the intake manifold is provided by a pressure sensor (PMAN) 300. Typically, the pressure sensor 300 measures a vacuum for a conventional engine, which could be a positive pressure when the system is operated in conjunction with a turbocharger. The intake manifold temperature is provided by a temperature sensor (TA) 302, which is connected to the intake manifold 266. The position of the butterfly valve 264 is provided by a position sensor (θth) 306. The temperature of the catalytic converter is measured by a temperature sensor (TCAT) 308. The CPU 288 incorporates the full sensor system as described hereinabove and is operable to predict the emissions emitted by the internal combustion engine which, in the preferred embodiment, are primarily NOx, and either output this information in the form of a display, store it as a history or utilize it to control the operation of the engine.

When controlling the operation of the engine, an emissions control system 308 is provided, which is operable to control certain parameters of the system. For example, one parameter that could be controlled is the internal threshold to the CPU 288 that determines the air-fuel ratio. Typically, the oxygen sensor 286 operates on a threshold such that when it is above the threshold, the air-fuel mixture is changed in one direction and, when the oxygen sensor falls below the threshold, the air-fuel ratio is changed in the other direction. By changing the threshold, the average air-fuel ratio will be changed, and therefore, the actual emissions output can also be changed. This will be described in more detail hereinbelow.

For systems that require emissions monitoring, there are a number of methods that have been employed in the past. One method that has been accepted by the Environmental Protection Agency (EPA) is to have a dashboard light that will illuminate after a predetermined number of miles, which predetermined number of miles is determined empirically. When the light is illuminated, the vehicle must be taken in for inspection. With the emissions sensor of the present invention, the actual emissions can be predicted from the operation of the engine and the light illuminated, indicating that the predicted emissions levels have fallen below a predetermined threshold. These thresholds can be changed, depending upon the type of vehicle, the area of the country, etc. For example, most commercial vehicles have less stringent pollution standards and certain areas like Los Angeles, Calif. have very stringent standards. In this manner, different thresholds can be loaded into the CPU 288, which thresholds can be selected in accordance with predetermined criteria. Additionally, a history can be provided of the vehicle as to the emissions generated by the engine and this stored for downloading at a later time for the purpose of monitoring the operation of the vehicle and the associated engine.

Since the emissions prediction is achieved utilizing a model of the system which utilizes the sensor outputs as inputs to provide the predicted output, the model must be initially trained. This initial training operation can be done on a "generic" engine with a "standard" emissions monitor and the then the model parameters downloaded to a standard integrated circuit which is utilized for all vehicles. This assumes that the model trained on the generic system holds true with respect to all subsequent systems and the manufacturing tolerances associated therewith. However, even if the generic model does provide a true representation of all engines manufactured for a given type of engine in combination with a standard emissions monitor, the parameters of the engine will change over time. It may therefore be necessary to update the training. This can be achieved in two ways. In the first method, the emissions can be measured with an emissions sensor that is external to the vehicle and not an integral part thereof and this compared to the predicted emissions output. If an error exists that is too large, the system then can be retrained. The retraining can either be a complete retraining of the model or merely an update of the training weights. In any event, this requires an actual emissions sensor to be utilized. In a second method, the model can have a "bias" applied thereto to provide a slight offset. This also requires actual emissions to be monitored. The actual values are necessary to know how to adjust the bias.

Figure 14:
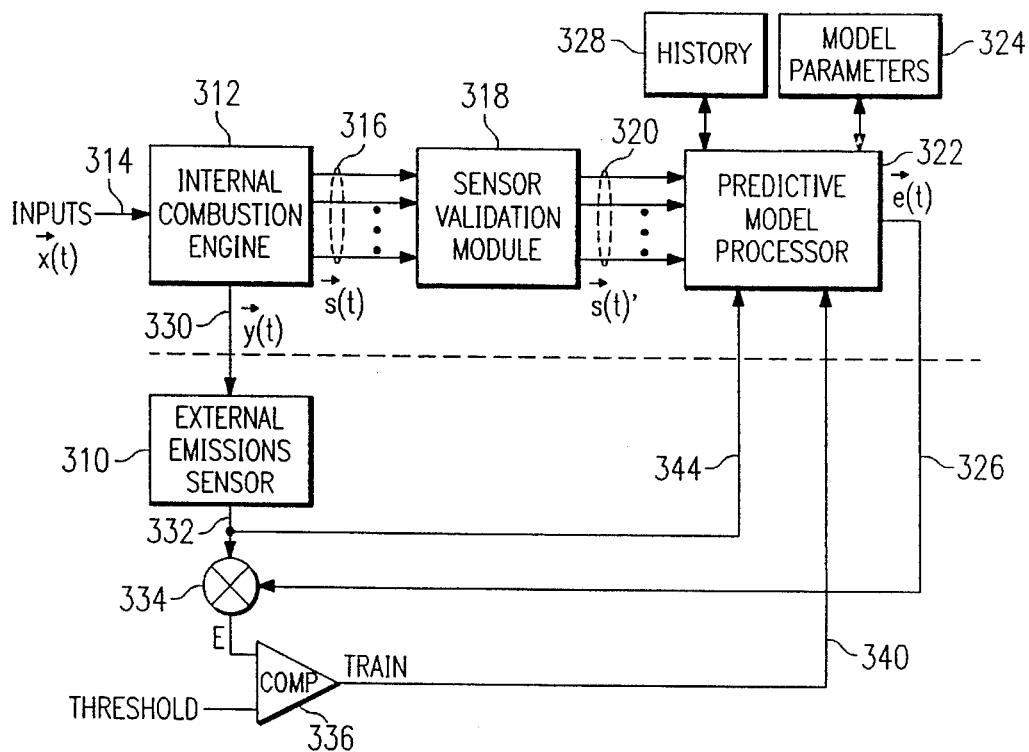
FIG. 14 illustrates a block diagram of a system wherein an external emissions sensor is utilized for training.

Referring now to FIG. 14, there is illustrated a block diagram of a system wherein an external emissions sensor 310 is utilized for training. The internal combustion engine is represented by a block 312, which receives inputs on a line 314 and provides measured outputs or state variables s(t) on lines 316, these comprising the inputs to the model. However, these state variables are first processed by sensor validation module 318, which was described hereinabove, and which is operable to substitute a predicted sensor output in the event of a failure of one of the sensors. This is described hereinabove with reference to FIGS. 7 and 8. The validated state variables s(t)' are output on lines 320 to a predictive model processor 322. The predictive model processor 322 is operable to interface with the memory 324 for storing model parameters to process the parameters and provide a predicted output e(t) on a line 326. Additionally, the predictive model processor 322 is operable to store a time history of the predicted output in a memory 328.

The model that is stored is a representation of the combined engine and emissions sensor. Therefore, the model will have associated therewith all aspects of both the engine and the emissions sensor. Even if the emissions sensor is inaccurate, the model is only as good as the sensor, but this inaccuracy must be incorporated into the model. This is important in that regulatory bodies require that the output measurement comply to their standards, which standards are defined by their equipment. If, for example, the emissions sensor that complied with their standards were in fact inaccurate, it would be important to predict an output with these inaccuracies. To correct these inaccuracies would not be acceptable. Therefore, the model is determined utilizing as part of the system the actual hardware sensor, which is removed during operation of the engine.

External to the internal combustion engine 312, the external emissions sensor 310 is connected to the output of the internal combustion engine, which comprises a line 330 labelled y(t). This represents the output of the system. This is merely the output of the exhaust pipe. The emissions sensor 310 is connected to the output to provide an actual output value of the emissions on a line 332. This is input to a difference device 334 to determine the difference between the output of the emissions sensor 310 and the predicted output on line 326. This generates an error E, which is input to a comparator 336. The comparator 336 compares the error E with a predetermined threshold and then outputs a "Train" signal on a line 340. If the error exceeds the threshold, a training operation is initiated. This is input to the predictive model processor 322. The predictive model processor 322 then enters into a training mode utilizing the actual emissions sensor outputs on a line 344 and the state variable inputs 320 to retrain the model. These parameters are then input to the memory 324. After training, the system will again be validated by comparing the operation of the internal combustion engine and the emissions output thereby with the predicted emissions output. Once the error has been minimized, i.e., reduced below the threshold, the system will be "validated". The predictive model processor 320 can train the network by two methods. In the first method, it can completely regenerate model parameters from scratch utilizing a typical training algorithm. In the second method, it can merely update the model parameters, i.e., provide a minor adjustment thereto in order to reduce the error.

Figure 15:
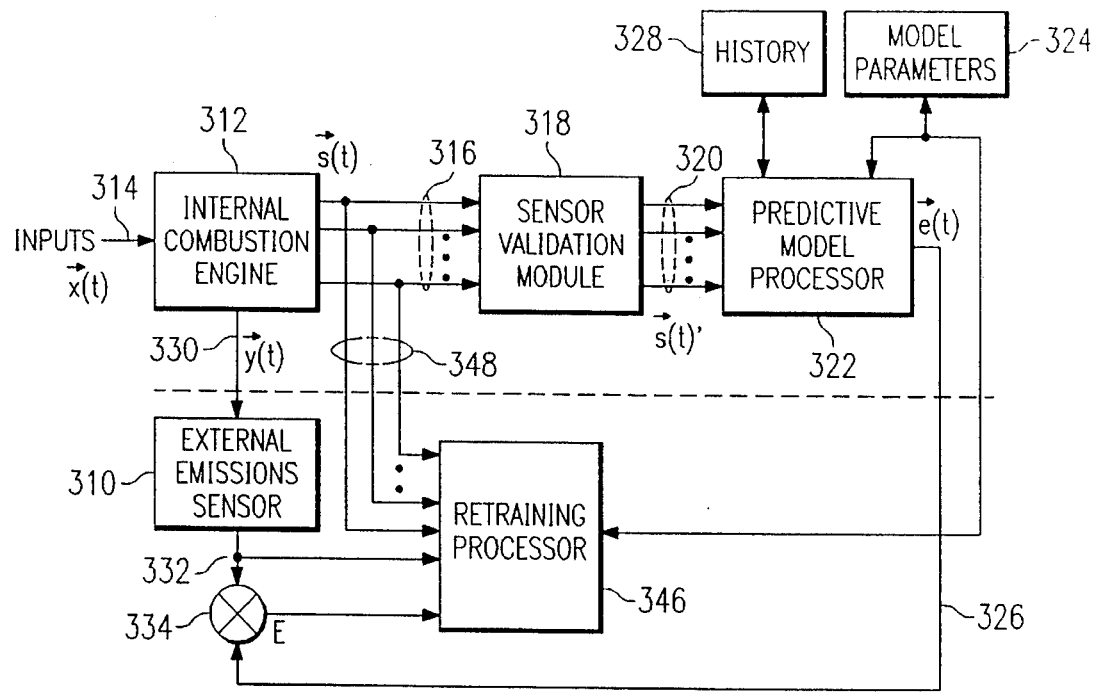
FIG. 15 illustrates an alternate method wherein the retraining operation is done external to the system with a retraining processor.

Referring now to FIG. 15, there is illustrated an alternate method wherein the retraining operation is done external to the system with a retraining processor 346. The retraining processor 346 is operable to receive on the input thereof the output state variables from the internal combustion engine 312 on lines 348, the actual output emissions sensor on the line 332 and the error output of the difference device 334. The retraining processor 346 then determines whether retraining is necessary, and if so, the retraining processor 346 will either update the model parameters or generate a new set of model parameters. During an update process, the old model parameters from the memory 324 are uploaded and adjusted and then downloaded back to the memory 324. In the complete training process, completely new model parameters are generated and then downloaded to the memory 324. Of course, after retraining or any modification of the model parameters 324, the system is again checked.

In the training of the network, one technique that can be utilized is backpropagation, as described in D. E. Rumelhart, G. E. Hinton, and R. J. Williams, "Learning Internal Representations by Error Propagation" in D. E. Rumelhart & J. L. McClelland, *Parallel Distributed Processing*, Vol. 1, 1986. In this technique as applied to a neural network, training is achieved by minimizing the Least Mean Square Errors with backpropagation. This utilizes the technique of steepest descents, wherein the weights $W_{ij}$ of a neural network and the parameters associated with the activation function are varied to minimize the error function. This backpropagation technique is essentially a common, non-linear least squares algorithm. It is a natural, non-linear extension of the linear nets commonly used in adaptive signal processing. Use of the chain rule in computing derivatives of the error generated during the training procedure provides useful interpolation to the minimization process and allows an easy generalization to multi-layers of non-linear units in a neural network. For one or more output units, the error output is minimized to:

$$E = \frac{1}{2} \sum_{i=0}^{M} (z_i(t) - y_i(t))^2 \quad (6)$$

where:

y(t)=output of a neural net; and z(t)=specified target output for a given output pattern.

For a network that contains non-linear hidden units, the term y(t) contains contributions from the outputs of hidden units in a hidden layer. Because the hidden layer has a non-linear transfer function, the output of the hidden layer will be an output of the non-linear function of its input and the error E becomes a square of non-linear function weights since the hidden layer outputs are fed into the topmost output layer in a conventional three layer neural network. The backpropagation algorithm is described in the literature and also described in U.S. Pat. No. 5,113,483 issued May 12, 1992 and entitled "Network with Semi-Localized Non-Linear Mapping of the input Space". This patent is incorporated herein by reference.

In addition to backpropagation, other techniques for training a neural network can be utilized, such as radial basis functions or Gaussian bars. Further, it is not necessary to utilize a neural network to provide a stored representation of the system. A fuzzy system (which is very similar to a radial basis function network) can also be utilized.

Figure 16:
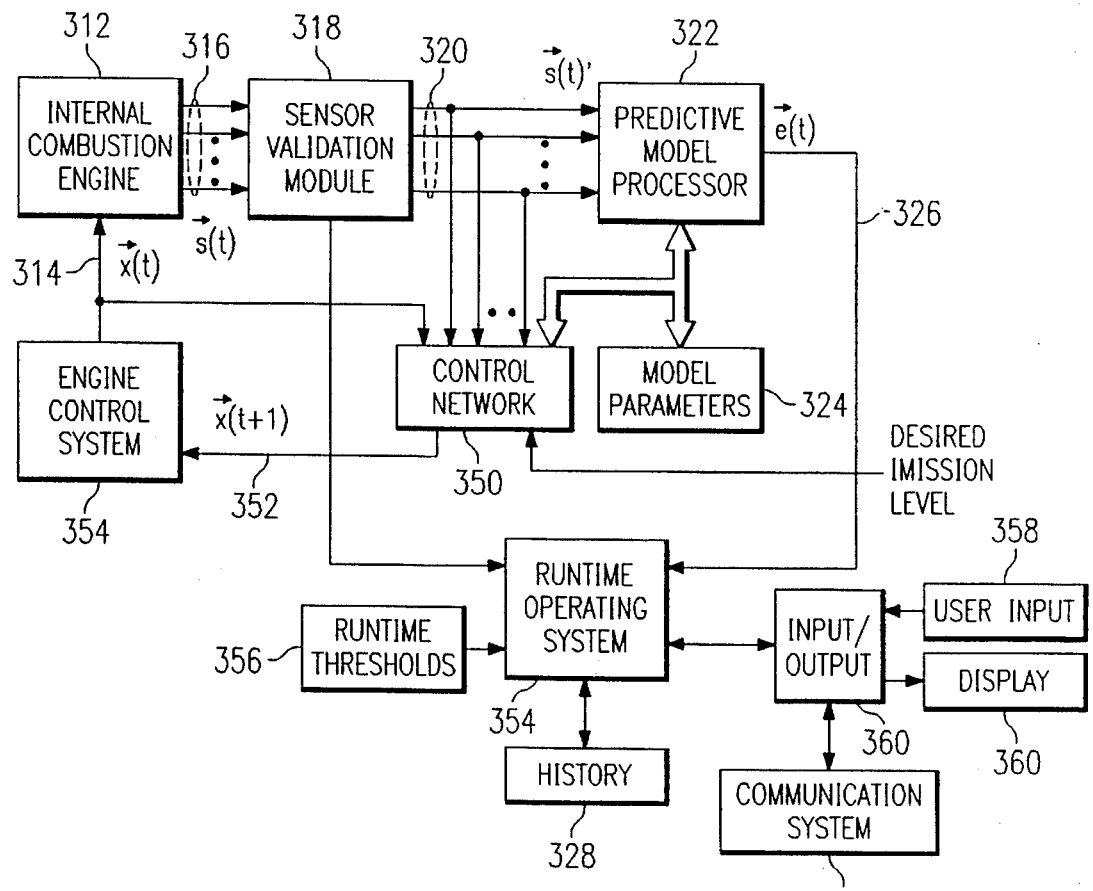
FIG. 16 illustrates a block diagram depicting the runtime operation of the internal combustion engine.

Referring now to FIG. 16, there is illustrated a block diagram depicting the runtime operation of the internal combustion engine 312. The system of FIG. 16 utilizes a control network 350 which is operable to receive the control input x(t) on line 314, the validated sensor outputs s(t)' on lines 320 and output updated control inputs x(t+1) on a line 352. The control network 350 is described above with reference to FIG. 5a and can actually incorporate the model that is implemented by the predicted model processor. A desired or target emissions level is input thereto. The line 352 is input to an engine control system 354 which is operable to effect the various controls on the internal combustion engine. Any one of the controls can be manipulated to control the emissions within predetermined guidelines, these controls associated with controlling he air-fuel ratio.

The overall system is controlled by a runtime operating system 354 which is operable to receive the predicted output on the line 326 from the predictive model processor 322 and also receive the output of the sensor validation module 318 indicating which, if any, of the sensors have been determined to be in error. This information, in addition to the predicted emissions value output on line 326 is then utilized by the runtime operating system to either store it in the memory 328 associated with the historical information or make various decisions as to what should be done with respect to the predicted emissions information.

Runtime thresholds are prestored in a memory 356 and are utilized by the runtime operating system for comparison with the predicted emissions. If the predicted emissions exceed the selected one of the thresholds, some action must be taken. For example, emissions may be acceptable at one threshold in one area of the country and unacceptable in another area of the country. Further, the predicted emissions levels may also have an acceptability that is a function of other parameters, such as temperature and humidity. The runtime thresholds could be selected as a function of atmospheric conditions or other criteria. However, in the preferred embodiment, it is anticipated that thresholds will be selected as a function of the locale that the engine is disposed in. Further, they could even be selected as a function of the time of day.

A user input 358 is utilized to select the thresholds or input thresholds via an input/output circuit 360. Further, the input/output circuit 360 is operable to interface with a display 360 and also with a communication system 362. The display 360 can be, for example, a warning light. Further, it could be some type of display that actually outputs an analog value in the form a "gas gauge" for viewing by the driver. This would allow the driver to actually view the emissions levels as a function of his driving conditions, etc. In one mode, the communications system 362 is provided such that industrial engines at remote sites can be controlled on a periodic basis to download the stored history information in memory 328 to a central station.

Figure 17:
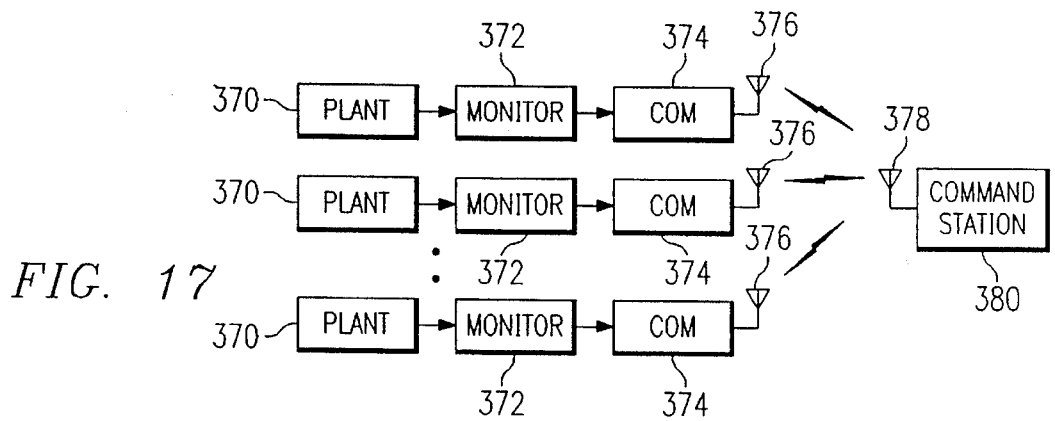
FIG. 17 illustrates an overall view of the communication system.

Referring now to FIG. 17, there is illustrated an overall view of the communication system. A plurality of engines referred to as plants 370 are disposed at remote locations, each having a virtual emissions monitor 372 associated therewith and each having a communications device 374 associated therewith. In the described embodiment, each of the communication devices 374 is operable to transmit information over a wireless communication path via an antenna 376, which antenna 376 can operate in both a receive mode and a transmit mode. The antennas 376 are operable to communicate with an antenna 378 on a command station 380. The protocol utilized for the transmission can be any type of conventional protocol. Although a wireless system is illustrated, it should be understood that a fixed wire system could be utilized.

Figure 18:
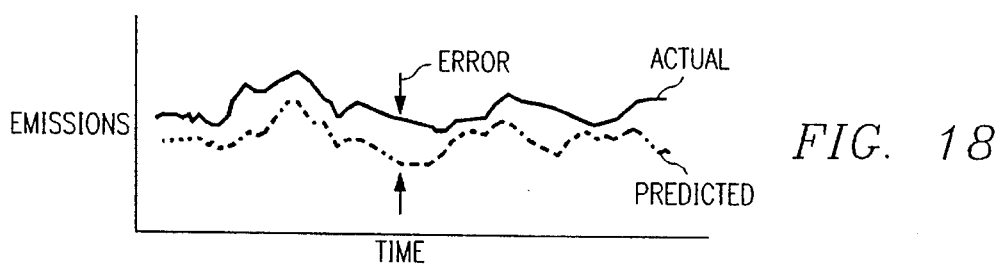
FIG. 18 illustrates a plot of the actual emissions output measured by an external emissions monitor and the predicted output from the virtual sensor.

In addition to training the system as described above utilizing techniques such as back propagation, Gaussian bars, radial basis functions, etc., the network could have the parameters thereof offset or a bias adjust applied thereto. After training a neural network in the normal manner, a situation could occur wherein the average of the plant output drifts by some amount. This situation is illustrated in FIG. 18, wherein a solid curve is illustrated representing the actual emissions output measured by an external emissions monitor and the dotted line represents the predicted output from the virtual sensor. It can be seen that there is an average error that occurs over time. This average error is determined and utilized to determine an offset, the average error defined as follows:

$$(\vec{e}) = (\vec{o}_a - \vec{o}_p) \qquad (7)$$

where:

$o_a$ is the actual plant output; and $o_p$ is the output value predicted by the model.

The averages are determined over all of the examples in some past window of time. Adding this average error to the model output results in the following:

$$\vec{o}_p{}' = \vec{o}_p + (\vec{e}) \qquad (8)$$

such that the new average error of the model is zero, as follows:

$$(\vec{e}') = (\vec{o}_a - \vec{o}_p{}') = (\vec{o}_a) - (\vec{o}_p) - (\vec{o}_a) + (\vec{o}_p) = 0 \qquad (9)$$

This bias adjustment must be made periodically or in an ongoing manner, utilizing moving averages.

In another parameter adjustment system, a first principles model could be utilized. First principle models are well-known and rely upon the fact that there are only a small number of controls that can be tuned or adjusted on the internal combustion engine. Typically, this tuning or control takes the form of adjusting parameters, i.e., co-efficients in the model to minimize the error that exists between the model output and the actual plant or engine output. This procedure is completely analogous to training a neural network model. The differences between the two training operations occur in the method that the parameters appear in the model and perhaps the way in which they are adjusted. First principle models are often simpler than neural network models in that they are often linear and have fewer adjustment parameters. An example of the first principle models applied to NOx emissions from an internal combustion engine is as follows:

$$NOx_{ppm} = k(T_c - T_m) \qquad (10)$$

where:

$T_c$ is the cylinder temperature;

$T_m$ is the manifold temperature and the average of the difference therebetween is taken over all cylinders; and k is the adjustable parameter.

The parameter k can be adjusted in the same iterative manner that one adjusts the parameters in a neural network model, i.e., by gradient descent; that is, one minimizes the overall error between the model and the plant as follows:

$$E = \frac{1}{2} \sum_{examples} (\vec{o}_a - \vec{o}_p)^2 = \frac{1}{2} \sum_{examples} e^2 \qquad (11)$$

via iteratively changing k according to the gradient descent equation:

$$\Delta K = -\eta \frac{\partial E}{\partial K} \qquad (12)$$

In the present case, this is simply:

$$\Delta K = \eta e (T_c - T_M) \qquad (13)$$

In the above equation, a simple control example would be a situation wherein if the NOx output was high, a signal would be issued that would result in reducing the air-fuel ratio by reducing the air and increasing the fuel.

Figure 19:
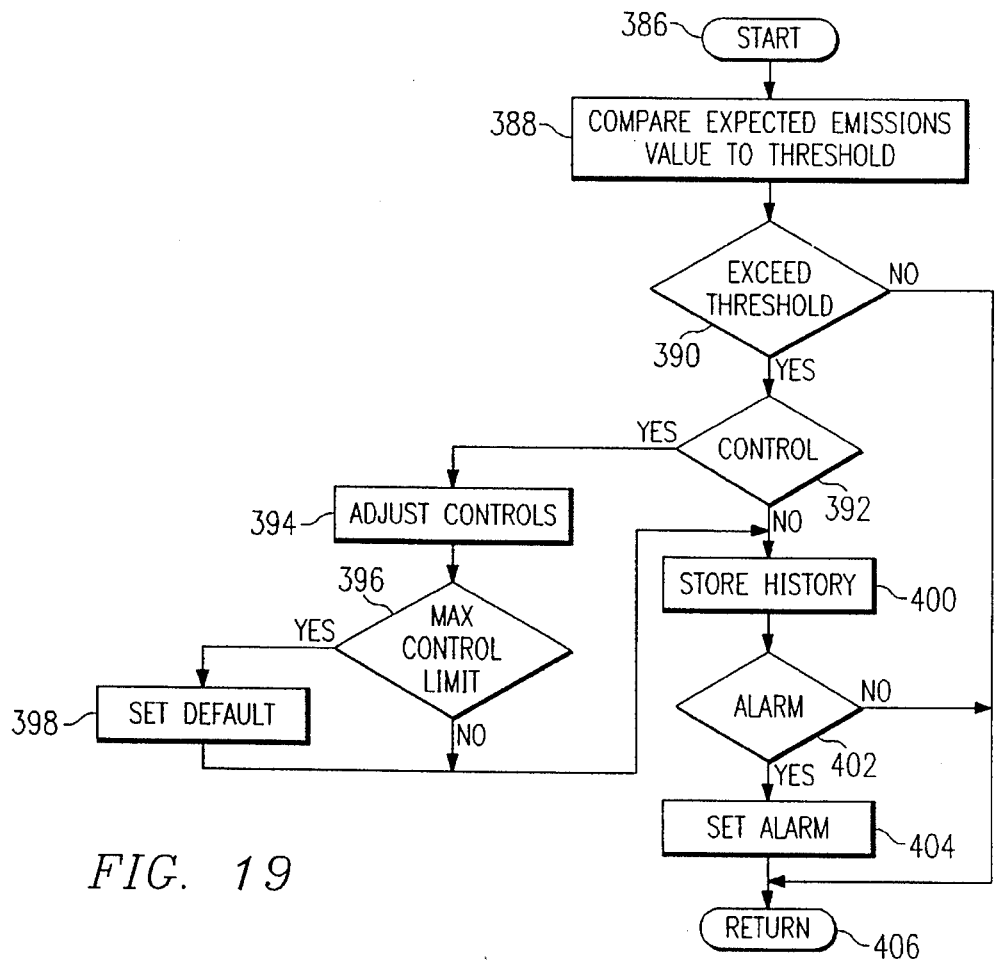
FIG. 19 illustrates a flowchart depicting the overall runtime control operation.

Referring now to FIG. 19, there is illustrated a flowchart depicting the overall runtime control operation. The program would be initiated at a start block 386 and then proceeds to a function block 388 to compare the expected emissions value to an internal runtime threshold, it being remembered that these thresholds can be selected by the user for a particular circumstance. The program then flows to a decision block 390 to determine if the expected or predicted emissions exceed the threshold. If so, this indicates that some control operation or failure mechanism must be performed. The program would flow to a decision block 392 to determine if a control operation is present. If so, the program would flow along a "Y" path to a function block 394 to adjust the controls in accordance with the predetermined control operation which could utilize the first principles operation as described above, or a control network. The program would then flow to a decision block 396 to determine if it is possible to effect an appropriate control. In order to determine this, maximum limits are set within the operating parameters of the engine by which the controls can be modified to reduce emissions. If these control limits are exceeded, the engine operation will deteriorate, even though the emissions was appropriate. If the maximum control limit has been exceeded, the program would flow along a "Y" path to a function block 398 to set the default settings for the emissions control parameters and then to a function block 400 to store the history. If the maximum control limit had not been exceeded the controls would be accepted and the program would flow along an "N" path from decision block 396 to the function block 400. If no controls were available, the program would also flow to the function block 400 from the decision block 392 along the "N" path thereof.

Once the history has been stored as to whether a control operation had been effected or a simple recording of the emissions history had been made, the program would flow to a decision block 402 to determine if an alarm operation were present. This could occur in the event that the comparison made at decision block 390 required an alarm to be set or if the presence of the default setting in the function block 398 required an alarm to be set. If an alarm is to be set, the program would flow along the "Y" path from decision block 402 to a function block 404 to set the alarm, this possibly being a light on the dashboard or an audible alarm. Further, this could be the existence of an alarm communication to a central station requiring a maintenance check. The program would then flow to a return block 406. If the alarm operation had not been present, the program would flow from the decision block 402 along the "N" path to the return block 406. Similarly, if the predicted emissions did not exceed the threshold, the program would flow to the return block 406 along the "N" path from the decision block 390.

Figure 20:
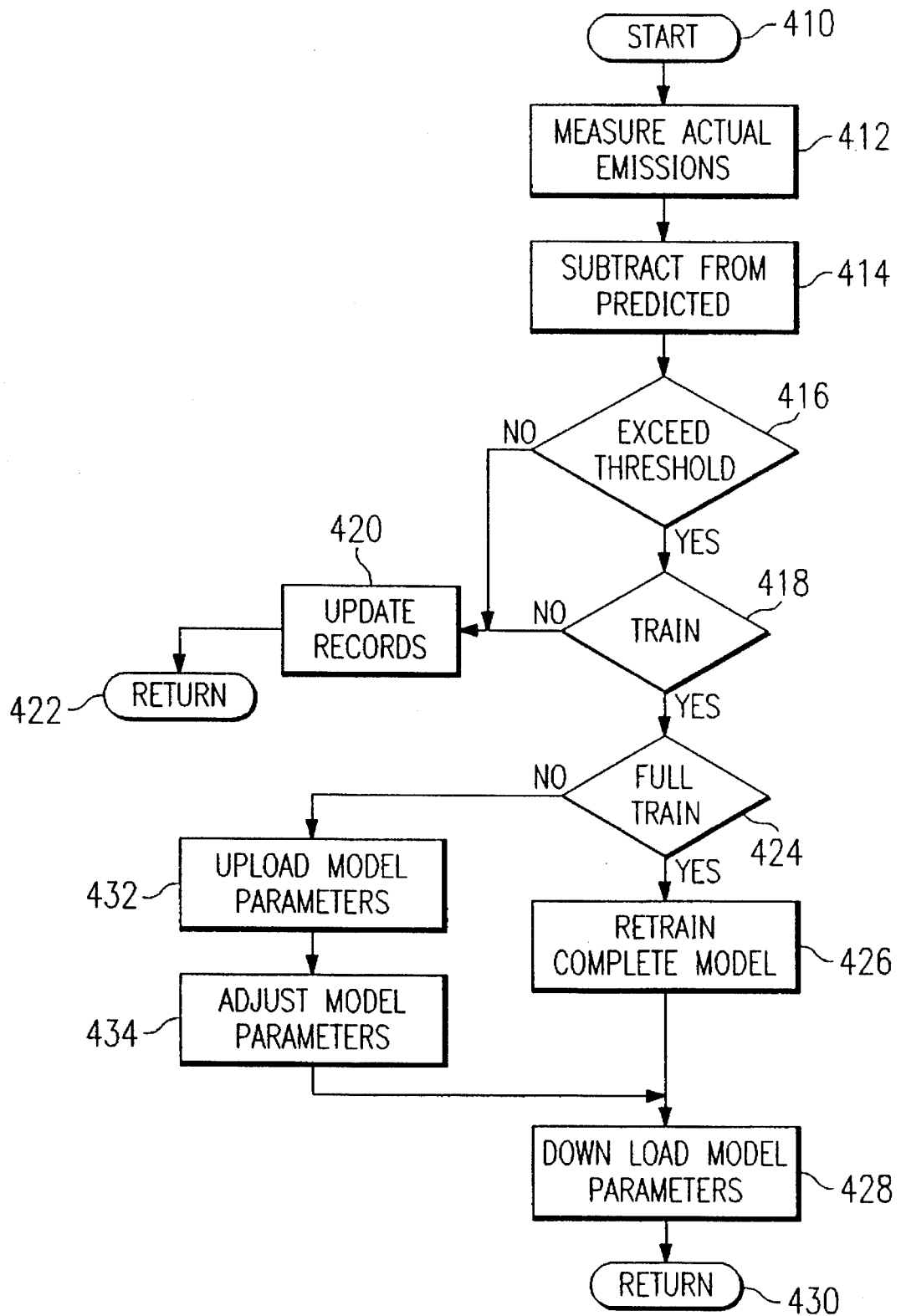
FIG. 20 illustrates a flowchart depicting the training operation.

Referring now to FIG. 20, there is illustrated a flowchart depicting the training operation. The program is initiated at a start block 410 and then proceeds to a function block 412 to measure the actual emissions. The program then flows to a function block 414 to compare the measured actual emissions to the expected or predicted value output by the virtual sensor. The program then flows to a decision block 416 to determine if the difference between the measured actual emissions and the predicted value exceed the threshold. If so, the program would flow along a "Y" path to a decision block 418 to determine if a training operation is to be performed. If not, the program would flow along an "N" path to a function block 420 to update a record database and then to a return block 422. Similarly, if the error did not exceed the threshold, the program would flow from the decision block 416 along the "N" path to the function block 420.

If a training operation is to be performed, the program would flow from the decision block 418 along a "Y" path to a decision block 424 to determine if a full training operation is to be performed. If yes, the program would flow along a "Y" path to a function block 426 to retrain a complete model and then to a function block 428 to download the model parameters back to the memory associated with the model parameters. The program will then flow to a return block 430. If a full training operation were not to be performed, i.e., a partial training operation only, the program would then flow along an "N" path from decision block 424 to a function block 432 to upload the model parameters that were in the system and then adjust these model parameters as indicated by a function block 434. After adjustment, the program would flow to the input of the function block 428 to download the model parameters. It should be understood that the training operation can be an on-board operation utilizing the model processor or an off-board operation utilizing an external processor.

In summary, there has been provided a system for predicting emissions in order to obviate the need for an actual emissions sensor on a reciprocating engine. The system utilizes a predictive model that is trained on various sensor outputs from the reciprocating engine with a target output of the actual emissions taken during generation of the training data set. Once trained, the system can operate without the actual emissions sensor, but represents the actual output of the emissions sensor. Periodically, the model can be checked to determine if the predicted value has deviated more than a predetermined amount from an actual measurement by performing an actual measurement with an external emissions sensor. If the measurement has deviated, the system can be indicated as out of spec or the network can be retrained.

Although the preferred embodiment has been described in detail, it should be understood that various changes, substitutions and alterations can be made therein without departing from the spirit and scope of the invention as defined by the appended claims.

What is claimed is:

1. A method for monitoring emissions in an internal combustion engine that emits noxious pollutants and provides a plurality of attached sensors for measuring select parameters of the engine operation as sensor output values, comprising the steps of:

storing in a predictive model a representation of the combined engine and a standard external emissions monitor, the standard external emissions monitor operable to measure the noxious pollutants output by the engine, the predictive model having an output that provides a prediction of the output of the standard external emissions monitor as a predicted emissions value and operable to receive as inputs select ones of the sensor output values;

inputting the select ones of the sensor output values to the predictive model; and predicting the output of the combined engine and external emissions monitor to provide an indication of the noxious pollutants output by the emissions monitor without requiring the standard external emissions monitor to be present on the engine.

2. The method of claim 1 and further comprising:

attaching an external emissions monitor substantially similar to the standard external emissions monitor to the engine;

comparing the output of the external emissions monitor to the predicted emissions value of the predictive model; and adjusting the stored representation in the predictive model whenever the predicted emissions value exceeds the actual output of the external emissions monitor by a predetermined amount.

3. The method of claim 2, wherein the stored representation in the predictive model is generated by training the predictive model on a training set of data comprised of actual sensor data received from the output of the sensors associated with the select ones of the sensor output values, and actual measured emissions output data from the external emissions monitor when connected to the engine.

4. The method of claim 3, wherein the step of adjusting comprises retraining the predictive model on a new set of training data utilizing the external emissions monitor to provide the actual output data.

5. The method of claim 3, wherein the step of adjusting comprises offsetting the predicted emissions value of the predictive model by a predetermined amount to minimize the error below a predefined level.

6. The method of claim 1, and further comprising:

comparing the predicted emissions value with an internal threshold value; and generating an alarm when the predicted emissions value exceeds the internal threshold value.

7. The method of claim 6, wherein the alarm is a light on a display.

8. The method of claim 6, and further comprising, storing a plurality of stored threshold values in a memory and selecting only one of the plurality of threshold values for the threshold value to utilize in the step of comparing, the step of selecting performed in accordance with predetermined criteria.

9. The method of claim 1, and further comprising, storing a history of the predicted emissions values output by the predictive model as a function of time.

10. The method of claim 8, and further comprising, downloading the stored history on a periodic basis.

11. The method of claim 1, and further comprising:

determining if the select measured parameters are outside of acceptable limits in accordance with predetermined criteria; and substituting a known value for the sensor output values when it is determined that they are outside of the acceptable limits.

12. The method of claim 11, wherein the step of substituting comprises predicting from a past history of the measured sensor output values to be substituted, a predicted value, the predicted value comprising the known values.

13. The method of claim 12, wherein the past history is a function of the other measured sensor output values.

14. The method of claim 11, wherein the step of determining comprises:

providing a sensor validation predictive network having as an input the actual sensor values of the engine, the sensor validation predictive network having associated therewith a stored representation of each of the actual sensor output values as a function of the other of the actual sensor output values to provide on the output thereof a predicted sensor output value for each of the actual sensor values input thereto;

predicting with the sensor validation predictive network the predicted sensor output value; and comparing each of the differences of the input actual sensor output values in the predictive sensor output values with predetermined limits for those differences.

15. The method of claim 1, and further comprising:

comparing the predicted emissions value output by the predictive model with a desired emissions value;

providing an emissions control system for modifying the operation of the engine; and controlling the emissions control system to operate in such a manner as to reduce any error between the predicted emissions value and the desired emissions value.

* * * * *

UNITED STATES PATENT AND TRADEMARK OFFICE
CERTIFICATE OF CORRECTION

PATENT NO. : 5,539,638

DATED : July 23, 1996

INVENTOR(S) : Keeler, et al.

Page 1 of 3

It is certified that error appears in the above-indentified patent and that said Letters Patent is hereby corrected as shown below:

In the Abstract:

Line 1, delete "[(360)]".

Line 4, delete [(322)]".

Line 6, delete "[(324)]".

Line 9, delete "[(326)]".

Line 11, delete "[(328)]".

Line 12, delete "[(260)]".

Line 15, delete "[(310)]".

Line 19, delete "[(322)]".

Line 22, delete "[(322)]".

Line 23, delete "[(350)]".

UNITED STATES PATENT AND TRADEMARK OFFICE
CERTIFICATE OF CORRECTION

PATENT NO. : 5,539,638
DATED : July 23, 1996
INVENTOR(S) : Keeler, et al.

It is certified that error appears in the above-indentified patent and that said Letters Patent is hereby corrected as shown below:

Column 6, equation (4), replace $$\vec{E} = \sum_{t=1}^{M} (\vec{y}(t) - \vec{O}(t))^2$$

with $$\vec{E} = \sum_{t=1}^{M} (\vec{y}(t) - \vec{o}(t))^2$$

UNITED STATES PATENT AND TRADEMARK OFFICE
CERTIFICATE OF CORRECTION

PATENT NO. : 5,539,638
DATED : July 23, 1996
INVENTOR(S) : Keeler, et al

It is certified that error appears in the above-indentified patent and that said Letters Patent is hereby corrected as shown below:

Column 8, line 10, replace "Ax(t+1)" with --$\Delta x(t+1)$--.

Column 10, line 48, replace "$X_A^P(t)$" with --$X_n^P(t)$--.

Signed and Sealed this

Seventh Day of January, 1997

BRUCE LEHMAN

*Attest:*

*Attesting Officer*     Commissioner of Patents and Trademarks